(12) United States Patent
Joshi et al.

(10) Patent No.: US 7,614,568 B2
(45) Date of Patent: *Nov. 10, 2009

(54) DEVICE EMPLOYING GAS GENERATING CELL FOR FACILITATING CONTROLLED RELEASE OF FLUID INTO AMBIENT ENVIRONMENT

(75) Inventors: Ashok V. Joshi, Salt Lake City, UT (US); Truman Wold, Salk Lake City, UT (US); John J. McEvoy, Sandy, UT (US)

(73) Assignee: Microlin, LLC, Salt Lake City, UT (US)

( * ) Notice: Subject to any disclaimer, the term of this patent is extended or adjusted under 35 U.S.C. 154(b) by 607 days.

This patent is subject to a terminal disclaimer.

(21) Appl. No.: 10/868,203

(22) Filed: Jun. 14, 2004

(65) Prior Publication Data

US 2005/0023371 A1    Feb. 3, 2005

Related U.S. Application Data

(63) Continuation-in-part of application No. 10/709,440, filed on May 5, 2004, and a continuation-in-part of application No. 10/300,729, filed on Nov. 20, 2002, now Pat. No. 6,957,779, and a continuation-in-part of application No. 11/115,273, filed on Apr. 2, 2002, now Pat. No. 6,787,008, and a continuation-in-part of application No. 09/649,563, filed on Aug. 28, 2000, and a continuation-in-part of application No. 09/645,673, filed on Aug. 24, 2000, now Pat. No. 6,923,383.

(51) Int. Cl.
*A61L 9/04* (2006.01)
(52) U.S. Cl. .............................. 239/6; 239/34; 239/337; 239/356; 239/363; 222/386.5; 222/399
(58) Field of Classification Search ................ 239/337, 239/302, 356, 362, 363; 604/891.1, 145, 604/500, 502; 222/399
See application file for complete search history.

(56) References Cited

U.S. PATENT DOCUMENTS 446,953 A    2/1891 Robert (Continued)

FOREIGN PATENT DOCUMENTS

WO    WO-00/76645    12/2000
WO    WO-2004/020005    3/2004

OTHER PUBLICATIONS

Hwu, Davis D., PCT International Search Report for PCT/US05/23523, (Oct. 19, 2006), 1-3.

(Continued)

*Primary Examiner*—Dinh Q Nguyen
(74) *Attorney, Agent, or Firm*—David Fonda

(57) ABSTRACT

A device for controllably releasing a fluid into an ambient environment. According to a particular embodiment of the present invention, the device comprises a housing having a fluid compartment and an orifice compartment disposed adjacent thereto and in fluid communication therewith via an orifice. The fluid compartment contains the fluid for release to the ambient environment. The orifice compartment includes a fluid exit opening covered by a removable sealing element and contains an initial quantity of fluid when the device is in an inactivated state. A fluid restrictor is disposed adjacent the orifice to restrict fluid flow from the fluid compartment into the orifice compartment in the inactivated state. A gas-generating cell is in selective communication with the fluid compartment such that gas generated by the cell is directed into the fluid compartment when the device is in an activated state. A fluid membrane is disposed between the gas-generating cell and the fluid compartment that allows the gas generated by the cell to pass therethrough to the fluid compartment in the activated state while preventing fluid within the fluid container from passing therethrough to the cell in the inactivated state. The device is activated by removing the sealing element to allow the initial quantity of fluid to exit out of the orifice compartment via the fluid exit opening and activating the cell to generate gas and force fluid from the fluid compartment to the orifice compartment and out the fluid exit opening in a controlled manner.

29 Claims, 4 Drawing Sheets

U.S. PATENT DOCUMENTS

| | | | |
|---|---|---|---|
| 575,365 A | 1/1897 | Mayer et al. | |
| 806,844 A | 12/1905 | Rosenstock | |
| 957,449 A | 5/1910 | Walz | |
| 1,099,720 A | 6/1914 | Peck | |
| 1,921,821 A | 8/1933 | Higgins | |
| 2,219,959 A | 10/1940 | Laidley | |
| 2,236,525 A | 4/1941 | Davis et al. | |
| 2,481,296 A | 9/1949 | Dupuy | |
| 2,670,236 A | 2/1954 | Bradburn | |
| 2,801,879 A | 8/1957 | Dick | |
| 2,867,360 A | 1/1959 | Sharma | |
| 2,991,517 A | 7/1961 | Bundy | |
| 3,169,705 A | 2/1965 | Geiger | |
| 3,254,841 A | 6/1966 | Loncker | |
| 3,482,929 A | 12/1969 | Gentil | |
| 3,685,734 A | 8/1972 | Paciorak et al. | |
| 3,804,592 A | 4/1974 | Garbe et al. | |
| 4,017,030 A | 4/1977 | Coplan et al. | |
| 4,166,478 A | 9/1979 | Sugimura et al. | |
| 4,169,757 A | 10/1979 | Kirjavainen | |
| 4,294,778 A | 10/1981 | DeLuca | |
| 4,312,347 A | 1/1982 | Magoon et al. | |
| 4,339,079 A | 7/1982 | Sato et al. | |
| 4,399,942 A * | 8/1983 | Chand | 239/34 |
| 4,408,635 A | 10/1983 | Packer | |
| 4,427,030 A | 1/1984 | Jouwsma | |
| 4,468,220 A * | 8/1984 | Willbanks | 604/140 |
| 4,477,414 A | 10/1984 | Muramoto et al. | |
| 4,526,320 A | 7/1985 | von Philipp et al. | |
| 4,574,494 A | 3/1986 | Wiencek | |
| 4,621,768 A | 11/1986 | Lhoste et al. | |
| 4,632,310 A | 12/1986 | Konicek | |
| 4,697,549 A | 10/1987 | Hair | |
| 4,809,912 A | 3/1989 | Santini | |
| 4,871,544 A | 10/1989 | Eckenhoff | |
| 4,886,514 A | 12/1989 | Maget | |
| 4,917,301 A | 4/1990 | Munteanu | |
| 4,948,047 A | 8/1990 | Zembrodt | |
| 4,966,767 A | 10/1990 | Eckenhoff | |
| 4,969,874 A | 11/1990 | Michel et al. | |
| 4,995,555 A | 2/1991 | Woodruff | |
| 5,074,252 A | 12/1991 | Morgan, Jr. | |
| 5,196,002 A | 3/1993 | Hanover et al. | |
| 5,357,793 A | 10/1994 | Jouwsma | |
| 5,368,863 A | 11/1994 | Eckenhoff et al. | |
| 5,398,851 A * | 3/1995 | Sancoff et al. | 222/386.5 |
| 5,427,870 A | 6/1995 | Joshi et al. | |
| 5,437,410 A | 8/1995 | Babasade | |
| 5,454,922 A | 10/1995 | Joshi et al. | |
| 5,474,785 A | 12/1995 | Wright et al. | |
| 5,538,605 A | 7/1996 | Joshi et al. | |
| 5,567,287 A | 10/1996 | Joshi et al. | |
| 5,638,868 A | 6/1997 | Loran | |
| 5,681,435 A | 10/1997 | Joshi et al. | |
| 5,700,245 A * | 12/1997 | Sancoff et al. | 604/145 |
| 5,707,499 A | 1/1998 | Joshi et al. | |
| 5,714,160 A | 2/1998 | Magruder et al. | |
| 5,744,014 A | 4/1998 | Gordon et al. | |
| 5,765,751 A | 6/1998 | Joshi | |
| 5,785,688 A | 7/1998 | Joshi et al. | |
| 5,810,253 A | 9/1998 | Ohayon | |
| 5,855,761 A | 1/1999 | Joshi | |
| 5,899,381 A | 5/1999 | Gordon et al. | |
| 5,915,925 A | 6/1999 | North, Jr. | |
| 5,921,251 A | 7/1999 | Joshi | |
| 5,932,204 A | 8/1999 | Joshi | |
| 5,951,538 A * | 9/1999 | Joshi et al. | 604/500 |
| 5,954,268 A | 9/1999 | Joshi et al. | |
| 5,971,713 A | 10/1999 | North, Jr. | |
| 5,997,821 A | 12/1999 | Joshi | |
| 6,042,704 A | 3/2000 | Joshi et al. | |
| 6,045,055 A | 4/2000 | Joshi et al. | |
| 6,060,196 A | 5/2000 | Gordon et al. | |
| 6,082,117 A | 7/2000 | Funatsu et al. | |
| 6,109,539 A | 8/2000 | Joshi et al. | |
| 6,135,126 A | 10/2000 | Joshi | |
| 6,220,267 B1 | 4/2001 | Joshi | |
| 6,283,461 B1 | 9/2001 | Joshi et al. | |
| 6,289,241 B1 | 9/2001 | Phipps | |
| 6,378,780 B1 | 4/2002 | Martens, III et al. | |
| 6,415,808 B2 | 7/2002 | Joshi | |
| 6,527,012 B1 | 3/2003 | Weber | |
| 6,553,712 B1 * | 4/2003 | Majerowski et al. | 43/131 |
| 6,622,755 B2 | 9/2003 | Weber | |
| 6,715,300 B2 | 4/2004 | Longsworth | |
| 6,787,008 B2 | 9/2004 | Joshi et al. | |
| 6,813,944 B2 | 11/2004 | Mayer et al. | |
| 6,901,965 B2 | 6/2005 | Baltes et al. | |
| 7,048,009 B2 | 5/2006 | Verhaeghe | |
| 7,149,417 B2 | 12/2006 | Joshi et al. | |
| 2002/0158156 A1 | 10/2002 | Joshi et al. | |
| 2005/0218074 A1* | 10/2005 | Pollock | 210/637 |
| 2007/0001024 A1 | 1/2007 | Wold et al. | |
| 2008/0257915 A1 | 10/2008 | Wold | |

OTHER PUBLICATIONS

Hwu, Davis D., PCT Written Opinion of the International Searching Authority for PCT/US05/23523, (Oct. 19, 2006), 1-3.

Nguyen, Dinh Q., PCT International Search Report for PCT/US05/21022, (Mar. 26, 2007), 1-3.

Nguyen, Dinh Q., PCT Written Opinion of the International Searching Authority for PCT/US05/21022, (Mar. 26, 2007), 1-3.

Kim, Christopher S., Office Action for U.S. Appl. No. 09/649,563 sent Sep. 10, 2003, 1-5.

Kim, Christopher S., Office Action for U.S. Appl. No. 09/649,563 send Apr. 13, 2004, 1-6.

Kim, Christopher S., Office Action for U.S. Appl. No. 09/649,563 sent Aug. 25, 2006, 1-6.

Kim, Christopher S., Office Action for U.S. Appl. No. 09/649,563 sent Jun. 12, 2007, 1-7.

Joshi, et al., Application for U.S. Appl. No. 09/649,563, filed Aug. 28, 2000, 1-33.

Nguyen, Office Action for U.S. Appl. No. 11/160,642 sent May 1, 2008, 1-7.

Kim, Office Action for U.S. Appl. No. 09/649,563 sent Feb. 15, 2008, 1-9.

Kim, Office Action for U.S. Appl. No. 09/649,563 sent Jul. 9, 2008, 1-8.

Varga, European Search Report for EP05790118.3 sent Nov. 7, 2007, 1-3.

Varga, Viktoria Communication pursuant to Article 94(3) EPC sent Aug. 20, 2008, 1-6.

Kim, Office Action for U.S. Appl. No. 09/649,563 sent Dec. 30, 2008, 1-8.

Nguyen, Office Action for U.S. Appl. No. 11/160,642 sent Dec. 10, 2008, 1-8.

* cited by examiner

DEVICE EMPLOYING GAS GENERATING CELL FOR FACILITATING CONTROLLED RELEASE OF FLUID INTO AMBIENT ENVIRONMENT

CROSS-REFERENCE TO RELATED APPLICATIONS

This application is a continuation-in-part of, and claims priority to, the following applications: application Ser. No. 09/645,673, entitled "Controlled Release of Substances," filed Aug. 24, 2000 now U.S. Pat. No. 6,923,383; application Ser. No. 09/649,563, entitled "Controlled Release of Substances," filed Aug. 28, 2000; application Ser. No. 10/115,273, entitled "Electrochemical Cell with Cathode Construction," filed Apr. 2, 2002 now U.S. Pat. No. 6,787,008; application Ser. No. 10/300,729, entitled "Foldable, Refillable Sustained-Release Fluid Delivery System," filed Nov. 20, 2002 now U.S. Pat. No. 6,957,779; and application Ser. No. 10/709,440 entitled "Moving Emanators," filed May 5, 2004.

TECHNICAL FIELD

This invention relates generally to fluid dispensing devices, and more particularly to fluid dispensing devices employing gas-generating cells as a propulsion component to facilitate controlled release of a fluid, such as, for example, a fragrance or sanitizer, into a surrounding environment.

BACKGROUND OF THE INVENTION

Various devices have been utilized as fluid dispensing apparatus, especially for fluids in liquid form, where the fluids are dispensed over an extended period of time at a predictable, substantially constant rate to the surrounding environment. One such device employs a gas-generating cell as a propulsion mechanism for the fluid.

One important aspect of such fluid delivery devices is shelf life of the device, particularly in high volume consumer applications, such as air freshener devices. In such applications, a shelf life of more than two years is typically required. Most known devices, however, are not designed for long shelf life, especially when they are mated to bladder-type fluid delivery reservoirs.

There are three major issues that affect shelf life of fluid delivery devices. First, shelf life is affected by the loss of moisture from the gas generating cell due to permeation through the gas chamber shell or through the flexible diaphragm. Since most of the reactions which generate hydrogen involve the consumption of water, desiccation of the cells typically will have a negative impact resulting in lower performance or shorter than desirable life. Second, if the gas generators are the type which consumes a metal, and oxygen is uncontrollably admitted to the cell, the metal will oxidize prematurely, and be spent when the device is to be activated. Third, if the gas generators are the type which consume a metal, hydrogen is generated to some degree prematurely. While corrosion inhibitors may be utilized to significantly reduce this effect, some hydrogen generation will occur if the active metal is in the presence of the aqueous solution, especially if the device is exposed to elevated temperature during storage. This hydrogen must be vented passively, otherwise the device will prematurely pressurize resulting in premature dispensing of the liquid, deformation of the device, or an undesirable burst of fluid delivery when the device is first activated.

Another concern exists with such fluid delivery devices that electrochemically consume a metal to form hydrogen in connection with the gas generator. With such devices, there is a delay before pumping of fluid occurs after the device is activated. This is caused by oxygen which has diffused into the headspace between the gas generating cell and the flexible diaphragm, which must be consumed before hydrogen generation begins.

There is yet another concern with such fluid delivery devices of the type which electrochemically consume a metal to form hydrogen. Typically, the metals utilized in such devices are amalgamated with mercury to reduce the amount of corrosion while being stored. This creates environmental concerns since mercury is toxic.

Among other things, the present invention is intended to address these as well as other shortcomings in the prior art and generally provides a device employing a gas-generating cell as a propulsion component to facilitate controlled release of a fluid to an ambient environment.

SUMMARY OF THE INVENTION

A device for controllably releasing a fluid into an ambient environment. According to a particular embodiment of the present invention, the device comprises a housing having a fluid compartment and an orifice compartment disposed adjacent thereto and in fluid communication therewith via an orifice. The fluid compartment contains the fluid for release to the ambient environment. The orifice compartment includes a fluid exit opening covered by a removable sealing element and contains an initial quantity of fluid when the device is in an inactivated state. A fluid restrictor is disposed adjacent the orifice to restrict fluid flow from the fluid compartment into the orifice compartment in the inactivated state. A gas-generating cell is in selective communication with the fluid compartment such that gas generated by the cell is directed into the fluid compartment when the device is in an activated state. A fluid membrane is disposed between the gas-generating cell and the fluid compartment that allows the gas generated by the cell to pass therethrough to the fluid compartment in the activated state while preventing fluid within the fluid container from passing therethrough to the cell in the inactivated state. The device is activated by removing the sealing element to allow the initial quantity of fluid to exit out of the orifice compartment via the fluid exit opening and activating the cell to generate gas and force fluid from the fluid compartment to the orifice compartment and out the fluid exit opening in a controlled manner.

According to other aspects of the invention, the device comprises a container or housing having three compartments and an emanator system located to receive fluid drop from the container. The first compartment of the container contains a gas-generating cell and is located at the top of the container. The second compartment contains a predetermined quantity of fluid and the third compartment contains a small initial amount of fluid to be dispensed at the start of the activation of the device. The emanator system is located just below the container. The emanator system volatizes the fluid dispensed from the container into the surrounding atmosphere.

The first and the second compartments are separated by either an impermeable member or a selectively permeable member. The impermeable member does not allow any fluid or its vapors within the second compartment to reach first compartment. It also does not allow gas generated by the gas generative cell to permeate into second compartment until such time that the pressure generated by the gas breaks the seal of the member and allows gas to put pressure on the fluid in second compartment. The selective permeable member allows only gas to permeate through but not allow fluid or its vapor in second compartment to permeate through to contact gas generating cell and associated electronics in the first compartment.

The second and the third compartments are separated by a plug or restrictor having an aperture configured in such a way that the fluid in second compartment will not drip under storage and gravity and will drip under gravity and gas pressure when the device is activated.

The third compartment has an opening in the bottom of the device. The third compartment contains a small initial amount of fluid. This compartment is sealed at the bottom opening by metal or plastic. The user of the device breaks the seal to get initial instant dose of fluid on to the emanator system to be volatilized into a surrounding atmosphere. The container of the device is positioned such that the first compartment is above second compartment and second compartment is above third compartment to allow gravity to help effectuate delivery of the fluid.

The emanator system is located so that fluid dripping from the container falls on emanator system, which volatizes or delivers the fluid to surrounding atmosphere.

According to other aspects of the invention, a means for holding and sealing a gas generating cell and associated electronics in the first compartment is provided so that gas generated by gas cell upon activation of the device puts pressure on the fluid in second compartment and does not escape out of first compartment when the device is activated. Means for protecting and separating gas generating and associated electronics from exposure to fluid or its vapor in the second compartment is also provided. Means for not allowing the fluid in second compartment to flow into third compartment under storage or inactivated conditions is also provided. Means for allowing the fluid in the second compartment to flow through third compartment out of container and on to emanator system under gravity and hydrogen gas pressure under an activated condition is also provided.

A predetermined quantity of initial fluid in the third compartment is dispensed instantaneously at the start of the activation of device and is released onto the emanator system to start the emanation of the fluid instantaneously while the fluid in the fluid compartment begins to flow.

A seal at the bottom opening of the container retains the fluid in the third compartment under storage and until such time a user of the device breaks the seal in order to get instantaneous release of fluid onto the emanator system located adjacent to a fluid exit opening of the third orifice compartment.

The emanator system comprises means for vaporizing the dispensed fluid to the surrounding atmosphere. The emanator systems may comprise mechanisms involving pleated high surface area paper emanators, generating cells, heated pads or elements, fans, vibrating elements or pads and combinations thereof.

These and other aspects of the present invention will be apparent after consideration of the written description, drawings and claims herein.

DETAILED DESCRIPTION OF THE PREFERRED EMBODIMENTS

Figure 1:
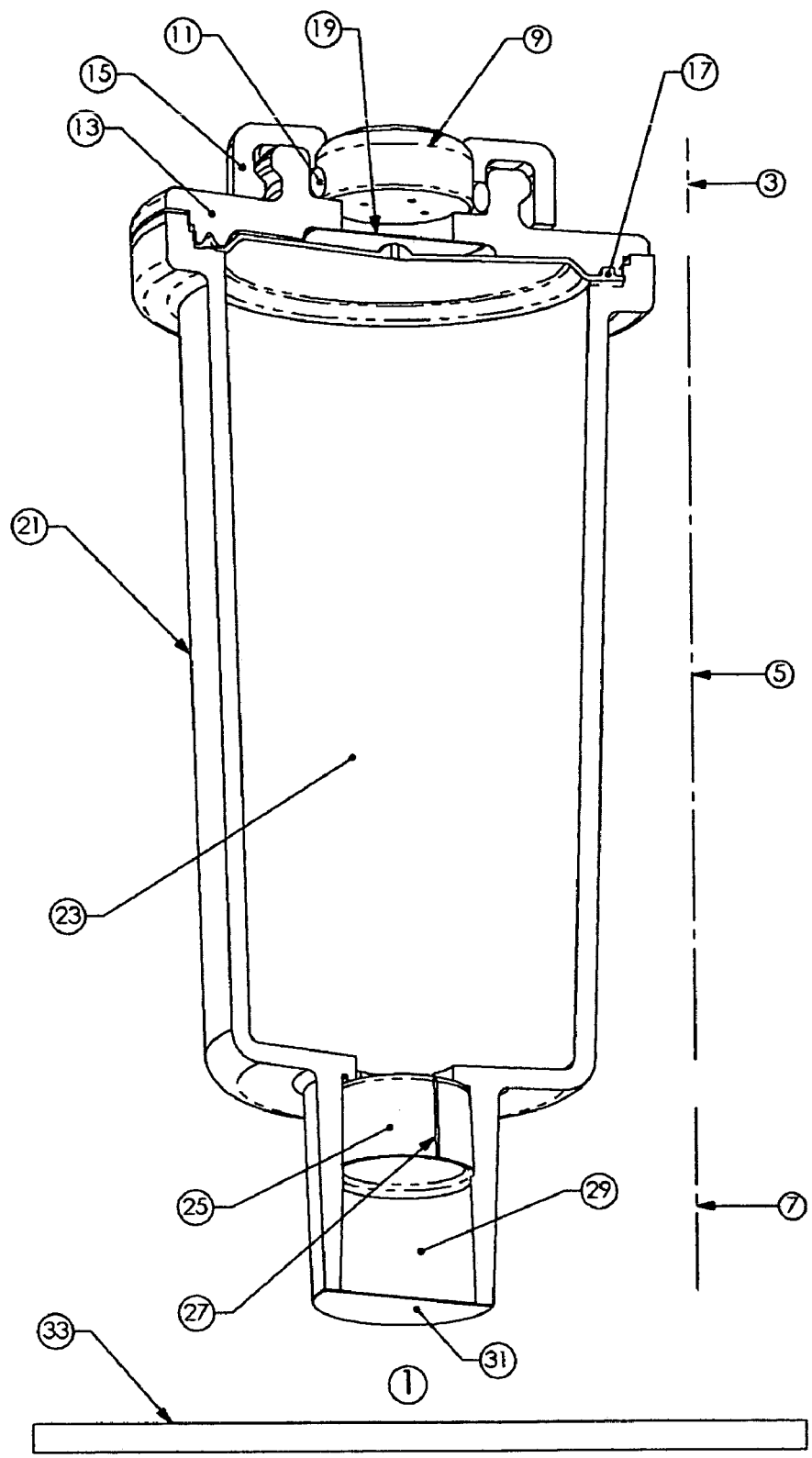
FIG. 1 is a schematic partial section view of an embodiment of a fluid delivery device in accordance with the principles of the present invention.

While the present invention is capable of embodiment in many different forms, there is shown in the drawings, and will herein be described in detail, one or more specific embodiments with the understanding that the present disclosure is to be considered an exemplification of the principles of the invention and is not intended to limit the invention to these specific embodiments.

Figure 2:
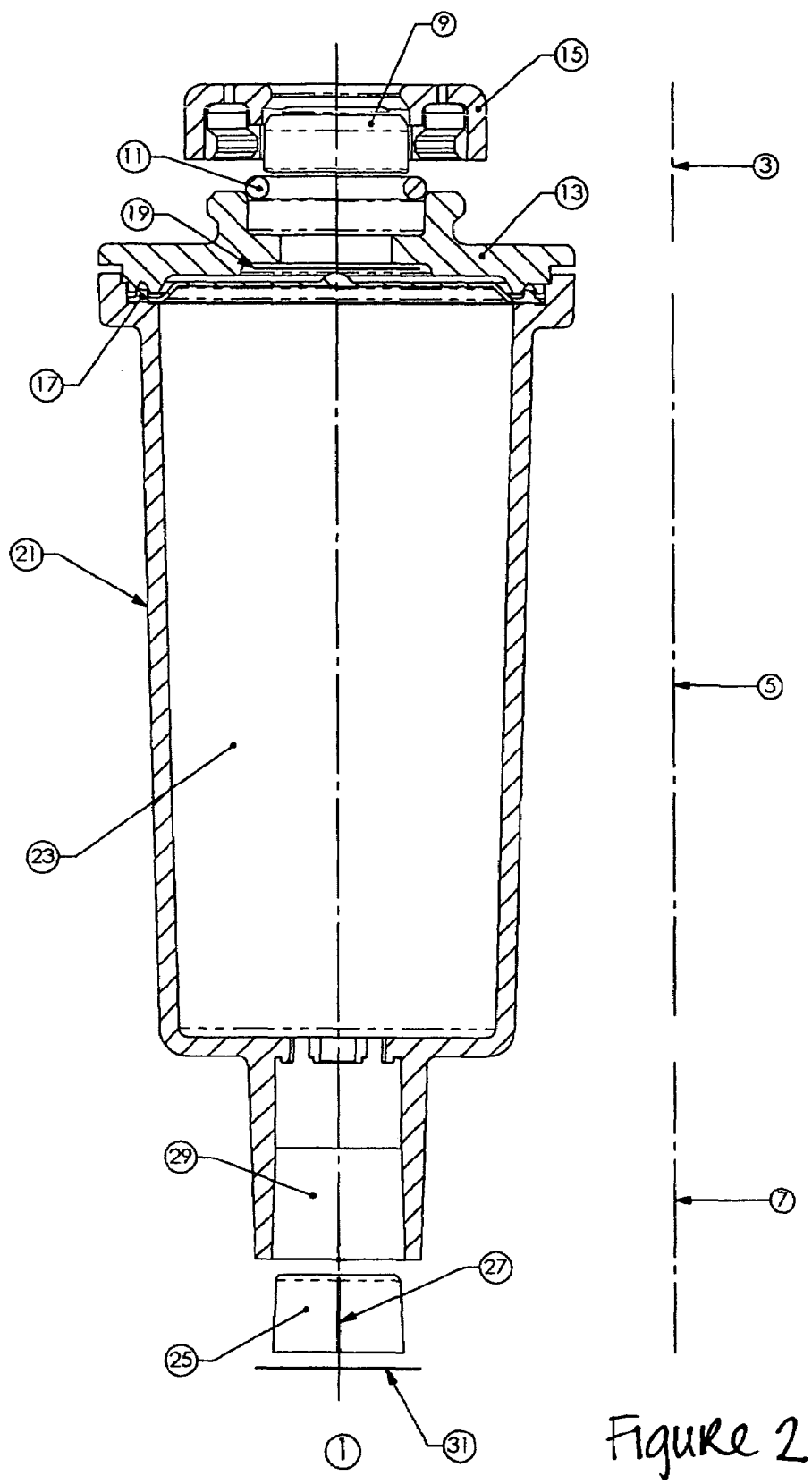
FIG. 2 is an exploded section view of the embodiment depicted in FIG. 1.

FIG. 1 depicts a particular embodiment of the device, shown in section view in order to illustrate the details of construction. FIG. 2 shows the preferred embodiment in an exploded section view. In this embodiment, the device has two main components, a fluid delivery container 1 and the emanation system 33. The container 1 is made up of three main sections, the gas generation compartment 3, the fluid compartment 5 and the orifice compartment 7.

The gas generation compartment 3 features a gas generating cell 9, held within the top cover 13. The top cover 13 is made of a material that is substantially impermeable to the gas being generated. The gas generating cell 9 is sealed to the top cover by an O-ring 11 or similar gas tight seal. The seal 11 prevents the gas generated by the cell 9 from escaping the container. The gas cell 9 is held in place within the top cover 13 by a retaining ring 15.

The retaining ring 15 and the top cover 13 can be connectable by a snap fit, press fit, screw threads or similar removable fit if it is desirable to be able to remove the gas cell 9 for recycling or disposal, or it could be a permanent method of joining such as gluing or heat staking. In addition, the retaining ring 15 could be made of a substantially electrically conductive material so that the surface of the retaining ring 15 can be used as the cathode contact for the gas generating cell 9. This is useful since the cathode surface of the gas generating cell 9 could be substantially covered by the seal 11. An electrically conductive retaining ring 15 can make contact with the top of the cathode portion of the gas generating cell 9 as it holds the cell in place, allowing the cathode contact of the switching mechanism to make contact with the retaining ring 15 anywhere on its surface. The anode contact area is found on the top surface of the gas generating cell 9.

The gas generating compartment 3 is situated adjacent to and above the fluid compartment 5, separated by a fluid membrane 17. The fluid membrane 17 is sealed to the top cover 13 preferably by a compression fit as shown in order to prevent fluid 23 from the fluid compartment 5 from entering the gas generating compartment 3 which could potentially damage the gas generating cell 9. The gas generating compartment 3 is attached to the fluid compartment 5 with a gas tight seal. The joint shown in FIG. 1 between the top cover 13 and fluid container 21 is an ultrasonic weld, but could be some other gas tight joint, including a one-piece integrated design.

As stated above, the fluid membrane 17 prevents fluid 23 from entering the gas generating compartment 3, but in addition it allows the gas being generated to pass through it into the fluid compartment 5. In the embodiment described, this is achieved by making the fluid membrane 17 from a material that is substantially permeable to the gas being generated. For example, if hydrogen is being generated by the gas generating cell 9 the fluid membrane 17 could be made of polypropylene.

An additional membrane, the gas membrane 19, may optionally be employed in this device. The gas membrane 19 is sealed to the top cover 13 in a gas tight arrangement. Its purpose is to protect the gas generating cell 9 from potentially harmful vapors from the volatile fluid 23 in the fluid compartment 5, and also to prevent the cell 9 from drying out before use. In the event that vapors from the fluid 23 could permeate through the fluid membrane 17, the gas membrane 19 will prevent them from coming into contact with the gas cell 9. In the event that it is desirable to partially assemble the fluid delivery container 1 with the gas cell 9 installed, and in case the gas cell 9 is subject to damage from drying out over time in this condition due to storage or environmental conditions, the gas membrane 19 will prevent water vapor from escaping the small gas generating compartment 3, thus preserving the integrity of the gas generating cell 9.

There are two preferable configurations for the gas membrane 19. First, it could be made of a material that is impermeable to the vapors from the fluid 23, but substantially permeable to the gas generated by the gas generating cell 9. In this embodiment the driving gas permeates freely through the gas membrane 19 as it is generated. Another embodiment is one in which the gas membrane is impermeable to both the vapors from the fluid 23 and the driving gas. In this case, the gas membrane 19 itself, or the joint between the gas membrane 19 and the top cover 13, is ruptured by the pressure developed by the driving gas once the gas cell 9 is activated. In both of these embodiments, the gas cell 9 is protected during storage of the device.

The fluid compartment 5 holds a predetermined amount of volatile fluid 23 to be dispensed within the fluid container 21. This compartment is situated adjacent to and above the orifice compartment 7 and is attached with a fluid tight seal, or made in an integrated one-piece configuration as shown in FIG. 1. The orifice compartment 7 is separated from the fluid compartment 5 by a restrictor 25. The restrictor 25 contains a tortuous path 27 for the fluid 23 to pass through. In the embodiment shown, the restrictor 25 has one or more grooves along its length to form the tortuous path(s) 27, and is sealed to the inside walls of the orifice compartment 7 with an interference fit.

The orifice compartment 7 contains a predetermined bolus of volatile fluid 29 that serves as an instant dose when the device is activated. The bolus 29 is sealed within the orifice compartment 7 by a removable membrane 31 covering a fluid exit opening of the compartment. This removable membrane 31 could be in the form of a screw cap that is removed just before use or, as shown in this embodiment, a thin metal foil seal that is punctured or peeled off just before use. Alternatively, a similar removable membrane could be employed.

To activate the fluid delivery container 1, a user breeches the removable membrane 31 in a prescribed manner, which allows the bolus of volatile fluid 29 to exit the orifice compartment 7. The user also applies an activation switch to the gas generating cell 9, connecting the anode and cathode of the cell 9 with a resistance, which begins gas generation within the cell 9. As the driving gas is generated by the gas generating cell 9, it passes through the gas membrane 19 and the fluid membrane 17 into the fluid compartment 5. Thus the driving gas applies pressure to the top of the fluid 23, driving it through the tortuous path 27 of the restrictor 25, and finally out of the orifice compartment 7.

As the volatile fluid 23 exits the fluid delivery container 1, it is directed onto the emanation system 33. The emanation system 33 can be a simple surface for the volatile fluid 23 to evaporate from, a wicking system to spread the fluid 23 to wick the fluid 23 up vertically over a large surface area, or a more active emanation system such as a fan, heater or ultrasonic vibrator.

Figure 3:
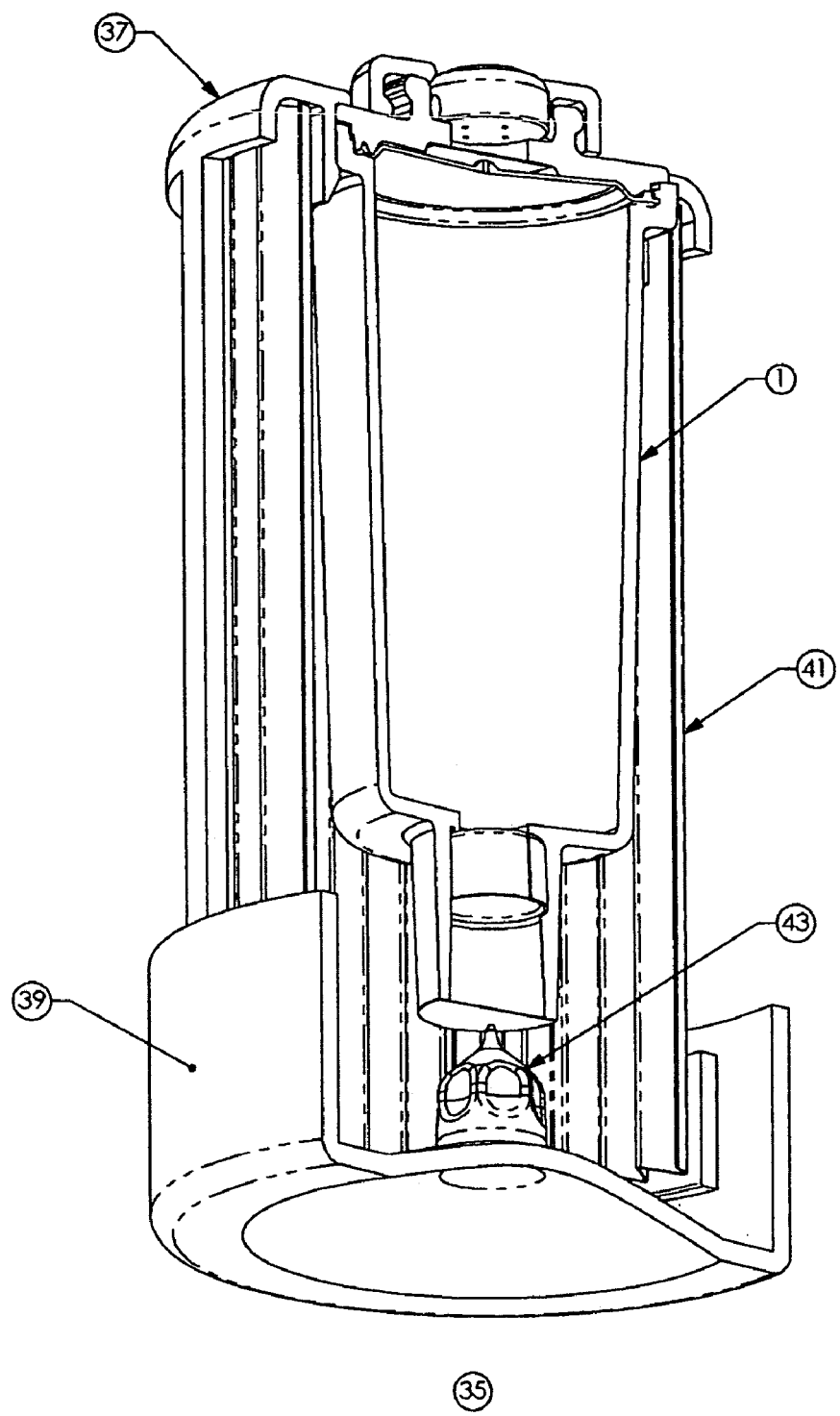
FIG. 3 is a schematic partial section view of an embodiment of a fluid delivery device in an inactivated state in accordance with the principles of the present invention.
Figure 4:
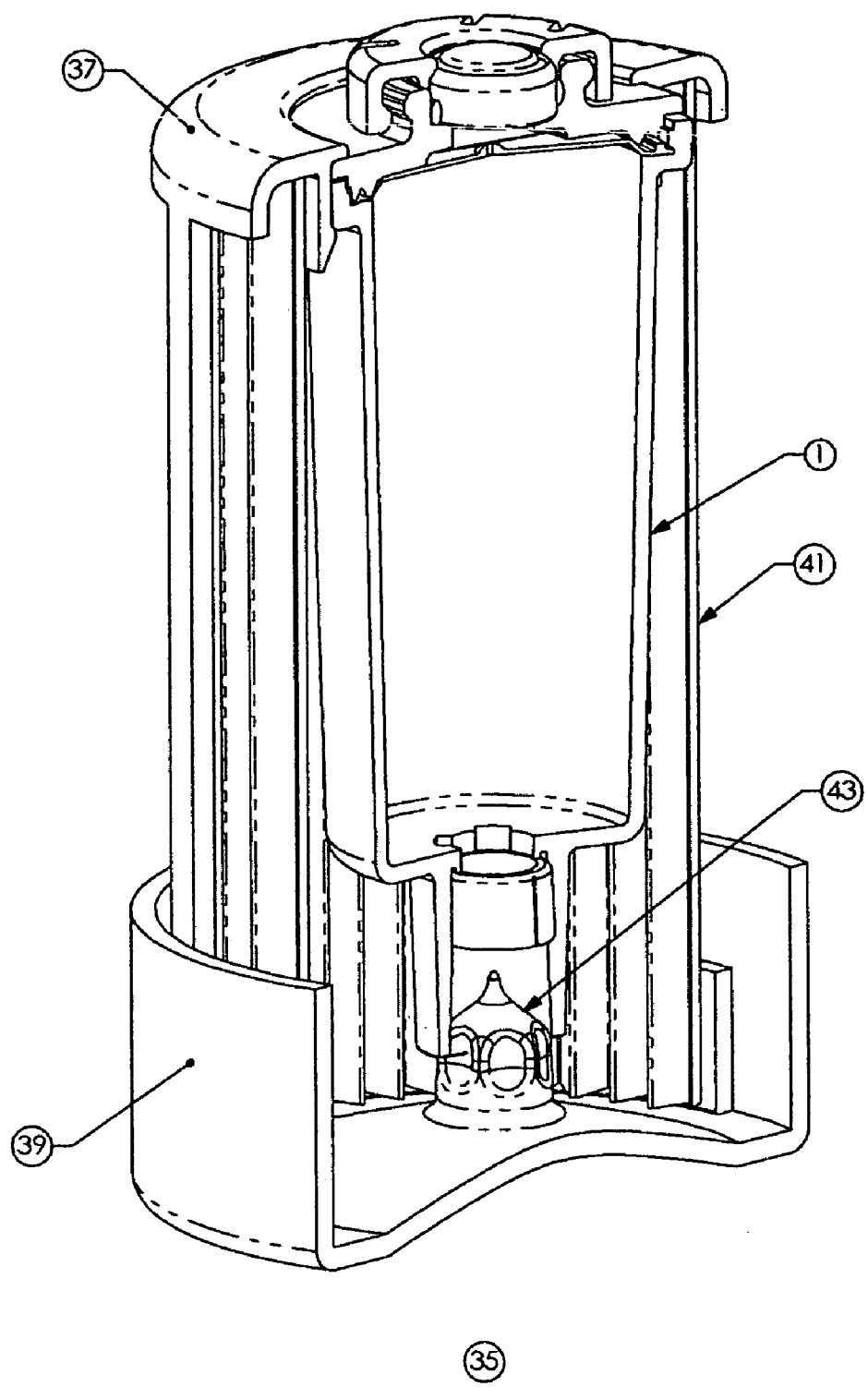
FIG. 4 is a schematic partial section view of the embodiment depicted in FIG. 3 in an activated state in accordance with the principles of the present invention.

FIG. 3 depicts a section view of one embodiment 35 of the emanation system with the fluid delivery container 1, shown prior to activation. FIG. 4 shows the same embodiment after activation. The fluid delivery container 1 is held to an upper emanator cage 37 with a snap fit configuration. A lower emanator cage 39 attaches to the upper emanator cage 37 with a vertically sliding fit. A wicking emanator pad 41 is held within the upper emanator cage 37 as well. The configuration of the emanator pad 41 shown is pleated in order to increase its surface area in order to increase the rate of fluid evaporation from its surface.

The lower emanator cage 39 contains a piercing element in the form of a pin 43. The pin 43 pierces the removable membrane 31 when the upper emanator cage 37 is pushed down into the lower emanator cage 39, as shown in FIG. 4. The bolus of volatile fluid 29 exits the orifice compartment 7, flowing down the surface of the piercing pin 43 to make contact with the emanator pad 41. The fluid is then wicked up the emanator pad 41 where it can evaporate into the environment. As the fluid 23 in the fluid compartment 5 is discharged from the fluid delivery container 1 by the driving gas from the gas generating cell 9, it follows the same path to the emanator pad and into the environment on a continuous basis.

While specific embodiments have been illustrated and described herein, numerous modifications may come to mind without significantly departing from the spirit of the invention, and the scope of protection is only limited by the scope of the accompanying Claims.

What is claimed is:

1. A device for controllably releasing a fluid into an ambient environment, the device comprising:
    a housing having a fluid compartment and an orifice compartment disposed adjacent thereto and in fluid communication therewith via an orifice, the fluid compartment containing a predetermined amount of fluid for release to the ambient environment, the orifice compartment including a fluid exit opening covered by a removable membrane and containing a separate predetermined amount of fluid when the device is in an inactivated state;
    a fluid restrictor disposed adjacent the orifice to restrict fluid flow from the fluid compartment into the orifice compartment in the inactivated state;
    a gas-generating cell in selective communication with the fluid compartment such that gas generated by the cell is directed into the fluid compartment when the device is in an activated state; and
    a fluid membrane disposed between the gas-generating cell and the fluid compartment that allows the gas generated by the cell to pass therethrough to the fluid compartment in the activated state while preventing fluid within the fluid container from passing therethrough to the cell in the inactivated state;
    wherein the device is activated by removing the sealing element to allow the predetermined amount of fluid in the orifice compartment to exit out of the orifice compartment via the fluid exit opening and activating the cell to generate gas and force the predetermined amount of fluid from the fluid compartment to the orifice compartment and out the fluid exit opening in a controlled manner.

2. The device of claim 1, wherein the fluid membrane comprises an impermeable seal that prevents gas generated from the cell to pass therethrough into the fluid compartment until sufficient pressure is generated to break the impermeable seal.

3. The device of claim 1, wherein the fluid membrane is a selectively permeable membrane that allows gas generated from the cell to pass therethrough into the fluid compartment while preventing fluid within the fluid container from passing therethrough to the cell.

4. The device of claim 1, further comprising an emanating system disposed adjacent the fluid exit opening to receive fluid from the fluid compartment in the activated state and deliver said fluid into the ambient environment.

5. The device of claim 1, wherein the removable membrane is a removable cap.

6. The device of claim 1, wherein the removable membrane is a pierceable membrane.

7. The device of claim 6, further comprising a moveable piercing element disposed adjacent the pierceable membrane to pierce the membrane when the device is activated.

8. A device for controllably releasing a fluid into an ambient environment, the device comprising:
- a housing including a gas compartment, a fluid compartment and an orifice compartment;
- the fluid compartment containing a predetermined amount of fluid for release to the ambient environment and in fluid communication with the orifice compartment via an orifice;
- the orifice compartment including a fluid exit opening covered by a removable membrane and containing a separate predetermined amount of fluid when the device is in an inactivated state;
- the gas compartment containing a gas-generating cell in selective communication with the fluid compartment such that gas generated by the cell is directed into the fluid compartment and applies pressure to the predetermined amount of fluid therein when the device is in an activated state;
- a fluid restrictor disposed adjacent the orifice to restrict fluid flow from the fluid compartment into the orifice compartment in the inactivated state; and
- a fluid membrane disposed between the gas-generating cell and the fluid compartment that allows the gas generated by the cell to pass therethrough to the fluid compartment in the activated state while preventing fluid within the fluid container from passing therethrough to the cell in the inactivated state; and
- a fluid emanator disposed adjacent the fluid exit opening to facilitate delivery of fluid to the ambient environment;
- wherein the device is activated by removing the removable membrane to allow the predetermined amount of fluid in the orifice compartment to exit out of the orifice compartment via the fluid exit opening to the emanator and activating the cell to generate gas and force fluid from the fluid compartment to the orifice compartment and out the fluid exit opening to the emanator in a controlled manner.

9. The device of claim 8, wherein the fluid membrane comprises an impermeable seal that prevents gas generated from the cell to pass therethrough into the fluid compartment until sufficient pressure is generated to break the impermeable seal.

10. The device of claim 8, wherein the fluid membrane is a selectively permeable membrane that allows gas generated from the cell to pass therethrough into the fluid compartment while preventing fluid within the fluid container from passing therethrough to the cell.

11. The device of claim 8, wherein the removable membrane is a removable cap.

12. The device of claim 8, wherein the removable membrane is a pierceable membrane.

13. The device of claim 12, further comprising a moveable piercing element disposed adjacent the pierceable membrane to pierce the membrane when the device is activated.

14. A device for controllable releasing a fluid into an ambient environment, the device comprising:
- a housing including a gas compartment, a fluid compartment containing a predetermined amount of fluid for release to the ambient environment, and an orifice compartment in fluid communication with the fluid compartment, the orifice compartment including a fluid exit opening covered by a removable membrane and containing a separate predetermined amount of fluid when the device is in an inactivated state;
- a gas-generating cell disposed within the cell compartment;
- means for holding and sealing the gas generating cell within the cell compartment such that gas generated by the cell when the device is in an activated state applies pressure to the predetermined quantity of fluid in the fluid compartment;
- means for protecting the gas generating cell from the fluid in the fluid compartment;
- means for preventing fluid in the fluid compartment from flowing into the orifice compartment in the inactivated state;
- means for allowing fluid in the fluid compartment to flow into the orifice compartment and out through the fluid exit opening in the activated state; and
- a fluid restrictor disposed adjacent the orifice to restrict fluid flow from the fluid compartment into the orifice compartment in the inactivated state;
- wherein the device is activated by removing the removable membrane to allow the predetermined amount of fluid to exit out of the orifice compartment via the fluid exit opening to the emanator and activating the cell to generate gas and force fluid from the fluid compartment to the orifice compartment and out the fluid exit opening in a controlled manner.

15. A device for controllably releasing a fluid into an ambient environment, the device comprising:
- a housing having a fluid compartment and an orifice compartment disposed adjacent thereto and in fluid communication therewith via an orifice, the fluid compartment containing a fluid for release to the ambient environment, the orifice compartment including a fluid exit opening;
- a fluid restrictor disposed adjacent the orifice to restrict fluid flow from the fluid compartment into the orifice compartment in the inactivated state;
- a gas-generating cell in selective communication with the fluid compartment such that gas generated by the cell is directed into the fluid compartment when the device is in an activated state;
- a fluid membrane disposed between the gas-generating cell and the fluid compartment that allows the gas generated by the cell to pass therethrough to the fluid compartment in the activated state while preventing fluid within the fluid container from passing therethrough to the cell in the inactivated state; and
- a gas membrane disposed between the gas-generating cell and the fluid compartment that prevents vapor from the fluid compartment to pass therethrough to the gas generating cell;
- wherein the device is activated by removing the sealing element to allow the initial quantity of fluid to exit out of the orifice compartment via the fluid exit opening and activating the cell to generate gas and force fluid form the fluid compartment to the orifice compartment and out the fluid exit opening in a controlled manner.

16. The device of claim 15, wherein the fluid membrane comprises an impermeable seal that prevents gas generated from the cell to pass therethrough into the fluid compartment until sufficient pressure is generated to break the impermeable seal.

17. The device of claim 15, wherein the fluid membrane is a selectively permeable membrane that allows gas generated from the cell to pass therethrough into the fluid compartment while preventing fluid within the fluid compartment from passing therethrough to the cell.

18. The device of claim 15, further comprising an emanating system disposed adjacent the fluid exit opening to receive the fluid from the fluid compartment in the activated state and deliver the fluid into the ambient environment.

19. The device of claim 15, wherein the removable membrane is a removable cap.

20. The device of claim 15, wherein the removable membrane is a pierceable membrane.

21. The device of claim 20, further comprising a moveable piercing element disposed adjacent the pierceable membrane to pierce the membrane when the device is activated.

22. A device for controllably releasing a fluid into an ambient environment, the device comprising:
   a housing including a gas compartment, a fluid compartment and an orifice compartment;
   the fluid compartment containing a fluid for release to the ambient environment and in fluid communication with the orifice compartment via an orifice;
   the orifice compartment including a fluid exit opening covered by a removable membrane and containing an initial quantity of fluid when the device is in an inactivated state;
   the gas compartment containing a gas-generating cell in selective communication with the fluid compartment such that gas generated by the cell is directed into the fluid compartment and applies pressure directly to the fluid therein when the device is in an activated state;
   a fluid restrictor disposed adjacent the orifice to restrict fluid flow from the fluid compartment into the orifice compartment in the inactivated state;
   a fluid membrane disposed between the gas-generating cell and the fluid compartment that allows the gas generated by the cell to pass therethrough to the fluid compartment in the activated state while preventing fluid within the fluid container from passing therethrough to the cell in the inactivated state;
   a gas membrane disposed between the gas-generating cell and the fluid compartment that prevents vapor from the fluid compartment to pass therethrough to the gas generating cell; and
   a fluid emanator disposed adjacent the fluid exit opening to facilitate delivery of the fluid to the ambient environment;
   wherein the device is activated by removing the removable membrane to allow the initial quantity of fluid to exit out of the orifice compartment via the fluid exit opening to the emanator and activating the cell to generate gas and force fluid from the fluid compartment to the orifice compartment and out the fluid exit opening to the emanator in a controlled manner.

23. The device of claim 22, wherein the fluid membrane comprises an impermeable seal that prevents gas generated from the cell to pass therethrough into the fluid compartment until sufficient pressure is generated to break the impermeable seal.

24. The device of claim 22, wherein the fluid membrane is a selectively permeable membrane that allows gas generated from the cell to pass therethrough into the fluid compartment while preventing fluid within the fluid container from passing therethrough to the cell.

25. The device of claim 22, wherein the removable membrane is a removable cap.

26. The device of claim 22, wherein the removable membrane is a pierceable membrane.

27. The device of claim 26, further comprising a moveable piercing element disposed adjacent the pierceable membrane to pierce the membrane when the device is activated.

28. A device for controllable releasing a fluid into an ambient environment, the device comprising:
   a housing including a gas compartment, a fluid compartment containing a fluid for release to the ambient environment, and an orifice compartment in fluid communication with the fluid compartment, the orifice compartment including a fluid exit opening covered by a removable membrane and containing an initial quantity of fluid when the device is in an inactivated state;
   a gas-generating cell disposed within the gas compartment;
   means for holding and sealing the gas generating cell within the cell compartment such that gas generated by the cell when the device is in an activated state applies pressure directly to the fluid in the fluid compartment;
   means for protecting the gas generating cell from the fluid in the fluid compartment;
   means for protecting the gas generating cell from vapor in the fluid compartment;
   means for preventing fluid in the fluid compartment from flowing into the orifice compartment in the inactivated state;
   means for allowing fluid in the fluid compartment to flow into the orifice compartment and out through the fluid exit opening in the activated state; and
   a fluid restrictor disposed adjacent the orifice to restrict fluid flow from the fluid compartment into the orifice compartment in the inactivated state;
   wherein the device is activated by removing the removable membrane to allow the initial quantity of fluid to exit out of the orifice compartment via the fluid exit opening to the emanator and activating the cell to generate gas and force fluid from the fluid compartment to the orifice compartment and out the fluid exit opening in a controlled manner.

29. A method for controllable releasing a fluid into an ambient environment, the method comprising:
   providing a device comprising a housing including a gas compartment, a fluid compartment containing the fluid for release to the ambient environment, and an orifice compartment in fluid communication with the fluid compartment, the orifice compartment including a fluid exit opening covered by a removable membrane, said gas compartment comprising a gas-generating cell;
   protecting the gas generating cell from the fluid in the fluid compartment;
   protecting the gas generating cell from vapor in the fluid compartment;
   restricting fluid flow from the fluid compartment into the orifice compartment in an inactivated state;
   removing the removable membrane to allow an initial quantity of fluid to exit out of the orifice compartment via the fluid exit opening to the emanator;
   activating the cell to generate gas; and
   directing the gas into direct communication with the fluid thereby forcing fluid from the fluid compartment to the orifice compartment and out the fluid exit opening in a controlled manner.

* * * * *